US012578546B2

(12) United States Patent
Qian et al.

(10) Patent No.: US 12,578,546 B2
(45) Date of Patent: Mar. 17, 2026

(54) SNAP ON MEDICAL INSTRUMENT FOR OPTICAL TRACKING

(71) Applicant: MediVis, Inc., New York, NY (US)

(72) Inventors: Long Qian, Brooklyn, NY (US); Christopher Morley, New York, NY (US); Osamah Choudhry, New York, NY (US); Jesse Harrison Gallant, New York, NY (US)

(73) Assignee: Medivis, Inc., New York, NY (US)

( * ) Notice: Subject to any disclaimer, the term of this patent is extended or adjusted under 35 U.S.C. 154(b) by 477 days.

(21) Appl. No.: 18/097,858

(22) Filed: Jan. 17, 2023

(65) Prior Publication Data

US 2024/0241343 A1     Jul. 18, 2024

(51) Int. Cl.
*G02B 7/182* (2021.01)
*A61B 90/00* (2016.01)

(52) U.S. Cl.
CPC .............. *G02B 7/182* (2013.01); *A61B 90/39* (2016.02); *A61B 2090/397* (2016.02)

(58) Field of Classification Search
CPC .... G02B 7/182; A61B 90/39; A61B 2090/397
See application file for complete search history.

(56) References Cited

U.S. PATENT DOCUMENTS

| | | | | |
|---|---|---|---|---|
| 7,137,712 B2 * | 11/2006 | Brunner | .................. | G02B 5/12 |
| | | | | 359/534 |
| 2012/0323247 A1 * | 12/2012 | Bettenga | .................. | A61F 2/46 |
| | | | | 606/91 |
| 2018/0207406 A1 * | 7/2018 | Ishida | ............... | A61M 25/0631 |
| 2021/0322107 A1 * | 10/2021 | Bratbak | ................ | A61B 34/20 |

* cited by examiner

*Primary Examiner* — Mariam Qureshi
(74) *Attorney, Agent, or Firm* — Cognition IP, P.C.; Edward Steakley; Justin White

(57) ABSTRACT

Various embodiments of a physical instrument are described herein. The physical instrument includes a main body with a top portion, a bottom portion, a first side and a second side. A first reflector and a first off-set reflector are each disposed on the top portion. The first reflector comprises a center region in alignment with a central axis of the main body, the central axis running from a first terminal end of the main body to a second terminal end of the main body. The first off-set reflector comprises a center region positioned according to a misalignment with the central axis of the main body. The first side includes an indentation and the second side includes a portion of a grip region with one or more grip ridges.

17 Claims, 3 Drawing Sheets

SNAP ON MEDICAL INSTRUMENT FOR OPTICAL TRACKING

BACKGROUND

Current conventional systems have limitations with regard to two-dimensional (2D) and three-dimensional (3D) images in surgical settings. Surgical planning and surgical navigation are necessary for every medical procedure. A surgeon and their team must have a plan for a case before entering an operating room, not just as a matter of good practice but to minimize malpractice liabilities and to enhance patient outcomes. Surgical planning is often conducted based on medical images including DICOM scans (MRI, CT, etc.), requiring the surgeon to flip through numerous views/slices, and utilizing this information to imagine a 3D model of the patient so that the procedure may be planned. Accordingly, in such a scenario, the best course of action is often a surgeon's judgment call based on the data that they are provided.

SUMMARY

Conventional systems are deficient with respect to infrared tracking of physical instruments.

Various embodiments of a physical instrument are described herein. The physical instrument includes a main body with a top portion, a bottom portion, a first side and a second side.

A first reflector and a first off-set reflector are each disposed on the top portion. The first reflector comprises a center region in alignment with a central axis of the main body, the central axis running from a first terminal end of the main body to a second terminal end of the main body. The first off-set reflector comprises a center region positioned according to a misalignment with the central axis of the main body.

The first side includes an indentation and the second side includes a portion of a grip region. The grip region may have one or more grip ridges. Along with the first side, the top surface may further include a portion of the grip region as well.

In some embodiments, a portion of the first side is shared between a portion of the groove of the bottom portion and at least a portion of the indentation Further areas of applicability of the present disclosure will become apparent from the detailed description, the claims and the drawings. The detailed description and specific examples are intended for illustration only and are not intended to limit the scope of the disclosure.

BRIEF DESCRIPTION OF THE DRAWINGS

The present disclosure will become better understood from the detailed description and the drawings, wherein.

DETAILED DESCRIPTION

Figure 1:
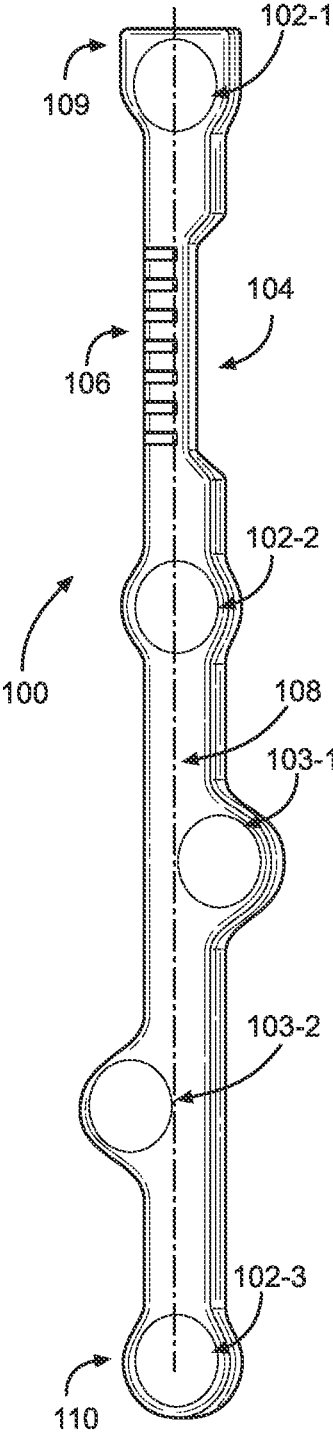
FIG. 1 is a diagram illustrating a type of perspective view of an exemplary embodiment.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

As shown in FIG. 1, according to various embodiments, a plurality of reflectors 102-1, 102-2, 102-3 and a plurality of off-set reflectors 103-1, 103-2 are disposed on a top surface 100 of the physical instrument. One or more of the reflectors 102-1, 102-2, 102-3 and the offset off-set reflectors 103-1, 103-2 may be made of a reflective material suitable for being tracked by an infrared camera(s).

A first side of the physical instrument includes an indentation 104 and a second side includes a grip region 106. The grip region 106 may include one or more grip ridges. Respective portions of each of the grip ridges may extend from the second side to the top surface 100 as well. The indentation 104 is formed by one or more portions of the first side of the physical instrument.

In one or more embodiments, the indentation 104 may have dimensions suitable for at least a portion of a human thumb to be positioned within the indentation 104. In some embodiments, the grip region 106 may have the dimensions and a number of grip ridges suitable for at least a portion of a human index finger to be positioned upon at least a portion of the grip region 106. It follows, then, that an individual, who is left-handed, may hold the physical instrument by performing and maintaining a pinched hand position with their thumb situated within the indentation 104 and their index finger placed upon the grip region 106. However, a right-handed individual will hold the physical instrument by performing and maintaining a pinched hand position with their thumb placed upon the grip region 106 and their index finger situated within the indentation 104.

The physical instrument has a defined central axis 108 that runs from a first terminal end 109 of the physical instrument to a second terminal end 110 of the physical instrument. Each reflector 102-1, 102-2, 102-3 includes a center and each respective reflector center is positioned on the top surface 100 in an alignment with the central axis 108. In some embodiments, one or more of the reflectors 102-1, 102-2, 102-3 may be disposed on the top surface 100 such that the central axis 108 bifurcates one or more of the reflectors 102-1, 102-2, 102-3. Each off-set reflector 103-1, 103-2 includes a center that is positioned on the top surface 100 in a misalignment with the central axis 108. In some embodiments, the central axis 108 does not bifurcate one or more of the off-set reflectors 103-1, 103-2.

In other embodiments, one or more of the off-set reflectors 103-1, 103-2 includes a center that is positioned on the top surface 100 in a misalignment with the central axis 108 such the central axis 108 may be positioned adjacent to an edge of one or more of the off-set reflectors 103-1, 103-2. In other embodiments, one or more of the off-set reflector 103-1, 103-2 includes a center that is positioned on the top surface 100 in a misalignment with the central axis 108 such the central axis 108 does not run through any portion of the one or more of the off-set reflectors 103-1, 103-2. In some embodiments, a first off-set reflector 103-1 may be more proximate to the first side than a second off-set reflector 103-2, whereby the second off-set reflector 103-2 may be more proximate to the second side than the first off-set reflector 103-1. In some embodiments, the central axis 108 is orientated such that it runs between a plurality of off-set reflectors 103-1, 103-2.

In other embodiments, respective portions of both the indentation 104 and the grip region 106 may be situated across from each other. In some embodiments, the indentation 104 and the grip region 106 may be situated across from each other in their entireties. In some embodiments, the entirety of the indentation 104 may be situated across from a portion of the grip region 106. In some embodiments, the indentation 104 may be situated across from the entirety of the grip region 106.

The indentation 104 and the grip region 106 may both be situated between a plurality of reflectors 102-1, 102-2. In other embodiments, the indentation 104 and the grip region 106 may both be situated between a plurality of off-set reflectors. In other embodiments, the indentation 104 and the grip region 106 may both be situated between a reflector and an off-set reflector.

Figure 2:
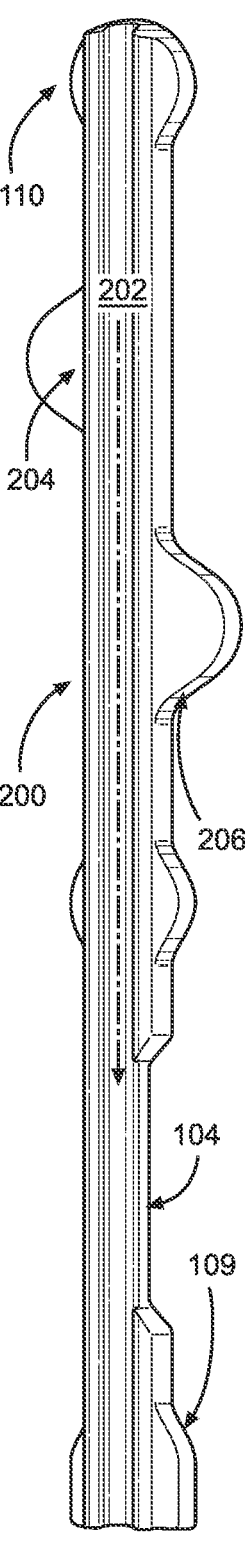
FIG. 2 is a diagram illustrating a type of perspective view of an exemplary embodiment.

As shown in FIG. 2, the physical instrument includes a bottom surface 200 with a groove 202 that runs along the bottom surface 200 from the first terminal end 109 to the second terminal end 110. In some embodiments, the groove 202 is aligned with the central axis 108 of the physical instrument. The bottom surface 200 includes a first bottom portion 206 that corresponds to the first off-set reflector 103-1 and a second bottom portion 204 that corresponds to the second off-set reflector 103-2.

The groove 202 has dimensions suitable for attaching another instrument to the physical instrument. For example, a tubular instrument may be attached to the physical as a result of inserting a portion of the tubular instrument within the groove 202. In some embodiments, dimensions of the groove 202 allow for the placement of at least a portion of a catheter within, along and throughout the groove 202. For example, dimensions of the groove 202 allow for at least a portion of a catheter to snap into the groove 202. In some embodiments, when a portion of catheter is positioned within the groove 202, an individual may hold the physical instrument while performing and maintaining a pinched hand position with their thumb (or index finger) situated within the indentation 104 and their index finger (or thumb) placed upon the grip region 106. By maintaining the pinched hand position, with respect to the indentation 104 and upon the grip region 106, the individual may thereby maintain control of the physical instrument in order to guide a catheter while it has been snapped into the groove 202. In addition, the indentation 104 further allows for an individual to place their thumb (or index finger) in the indentation 104 in such a manner that their pinched hand position will be in contact with both the physical instrument and the catheter (or any other type of instrument) while it has been snapped into the groove 202.

As the individual manipulates the physical instrument, the various changes to respective positions and orientations of the physical instrument are tracked via a camera tracking the reflectors 102-1, 102-2, 102-3, 103-1, 103-2. The respective positions and orientations of the physical instrument, tracked in reference to the reflectors 102-1, 102-2, 102-3, 103-1, 103-2, thereby serves as indications of a current placement and manipulation of the catheter as well. It is understood that dimensions of the groove 202 are not limited to being compatible with only tubular instruments. Various embodiments of the physical instrument may have a groove 202 with dimensions suitable for attaching the physical instrument to any instrument of any type of shape(s).

Figure 3:
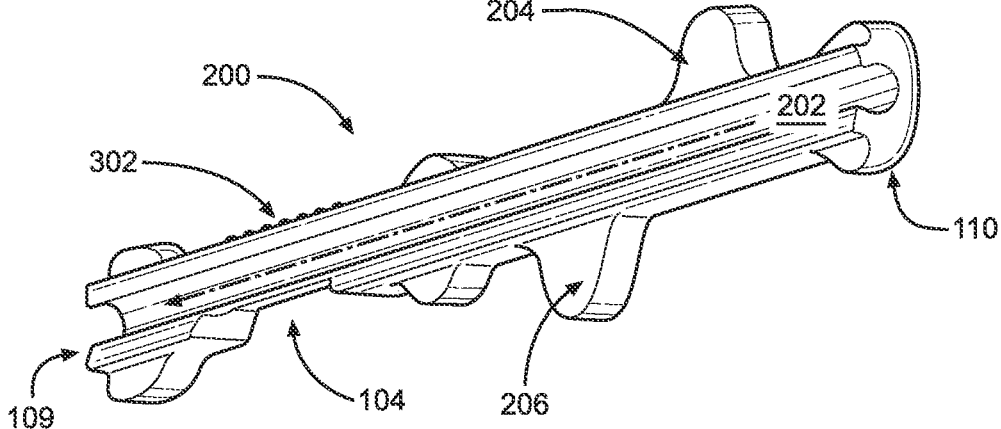
FIG. 3 is a diagram illustrating a type of perspective view of an exemplary embodiment.

As shown in FIG. 3, while one or more of the grip ridges of the grip region 106 may be disposed on the top surface 100, various portions of one or more of the grip ridges may extend to being disposed on at least a portion 302 of the second side. For example, one or more of the grip ridges of the grip region 106 may have a first ridge portion disposed on a portion 302 of the second side and also have a second ridge portion disposed on the top surface 100. In some embodiments, a terminus of one or more of the grip ridges of the grip region 106 may be positioned along the central axis 108. In some embodiments, a terminus of one or more of the grip ridges of the grip region 106 may not be positioned along the central axis 108.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A physical instrument comprising:
   a main body with a top portion, a bottom portion, a first side, a second side, a first terminal end, and a second terminal end, the main body defining a central axis extending from the first terminal end to the second terminal end, wherein the first side includes an indentation and the second side includes at least a portion of a grip region with one or more grip ridges;
   a first reflector disposed on the top portion, the first reflector including a center region disposed exactly on the central axis;
   a second reflector disposed on the top portion, the second reflector including a center region disposed exactly on the central axis;
   a third reflector disposed on the top portion, the third reflector including a center region disposed exactly on the central axis;
   a first off-set reflector disposed on the top portion, the first off-set reflector including a center region disposed at a distance from the central axis; and
   a second off-set reflector disposed on the top portion, the second off-set reflector including a center region disposed at a distance from the central axis to the opposite side of the first off-set reflector, wherein the main body, the one or more grip ridges, the center regions of the first, second, and third reflectors, at least a portion of the first off-set reflector, and at least a portion of the second off-set reflector are all disposed along the central axis.

2. The physical instrument of claim 1, wherein at least one reflector and at least one off-set reflector comprises a material suitable for optical tracking via at least one infrared camera.

3. The physical instrument of claim 1, wherein the first off-set reflector is situated between the first reflector and the second reflector.

4. The physical instrument of claim 1, wherein the first reflector is situated adjacent to the second reflector; and wherein the first off-set reflector is situated adjacent to the second reflector.

5. The physical instrument of claim 1, wherein a plurality of the off-set reflectors are situated between the first reflector and the second reflector.

6. The physical instrument of claim 1, wherein the indentation is situated between the first reflector and the second reflector.

7. The physical instrument of claim 1, wherein the grip region is situated between the first reflector and the second reflector.

8. The physical instrument of claim 1, wherein a portion of the indentation is situated across from a portion of the grip region.

9. The physical instrument of claim 1, wherein the first reflector is situated at the first terminal end.

10. The physical instrument of claim 9, wherein the second reflector is situated at the second terminal end.

11. The physical instrument of claim 9, wherein the first off-set reflector is situated at the second terminal end.

12. The physical instrument of claim 1, wherein a first portion of the grip region is disposed on the top surface.

13. The physical instrument of claim 12, wherein a second portion of the grip region is disposed on the second side.

14. The physical instrument of claim 1, wherein the bottom portion of the main body includes a groove extending the entire length of the main body from the first terminal end to the second terminal end and configured to accept therein at least a portion of a catheter.

15. The physical instrument of claim 1, wherein a portion of the first off-set reflector is more proximate to the first side than a portion of a second off-set reflector; wherein the portion of the second off-set reflector is more proximate to the second side than the portion of the first off-set reflector; and wherein the central axis comprises an orientation running the central axis between the first and the second off-set reflectors.

16. The physical instrument of claim 1, wherein the main body defines an elongated component along its central axis having a length that is at least five times greater than its width.

17. A physical instrument configured to be held by a user during a medical procedure, the physical instrument comprising:

a main body with a top portion, a bottom portion, a first side, a second side, a first terminal end, and a second terminal end, the main body defining a central axis extending from the first terminal end to the second terminal end, wherein the first side includes an indentation and the second side includes at least a portion of a grip region with one or more grip ridges;

a first reflector disposed on the top portion, the first reflector including a center region disposed exactly on the central axis;

a second reflector disposed on the top portion, the second reflector including a center region disposed exactly on the central axis;

a third reflector disposed on the top portion, the third reflector including a center region disposed exactly on the central axis;

a first off-set reflector disposed on the top portion, the first off-set reflector including a center region disposed at a distance from the central axis, wherein the main body, the center region of the first reflector, and at least a portion of the first off-set reflector are all disposed along the central axis;

a second off-set reflector disposed on the top portion, the second off-set reflector including a center region disposed at a distance from the central axis to the opposite side of the first off-set reflector, wherein the center regions of the second and third reflectors and at least a portion of the second off-set reflector are all disposed along the central axis; and a groove formed within and extending the entire length of the main body from the first terminal end to the second terminal end, wherein the groove is configured to accept therein at least a portion of a catheter.

* * * * *